US012648854B2

(12) United States Patent
Noda

(10) Patent No.: US 12,648,854 B2
(45) Date of Patent: Jun. 9, 2026

(54) ARTIFICIAL JOINT STEM

(71) Applicant: KYOCERA CORPORATION, Kyoto (JP)

(72) Inventor: Iwao Noda, Takatsuki (JP)

(73) Assignee: KYOCERA Corporation, Kyoto (JP)

( * ) Notice: Subject to any disclaimer, the term of this patent is extended or adjusted under 35 U.S.C. 154(b) by 803 days.

(21) Appl. No.: 17/927,598

(22) PCT Filed: May 29, 2020

(86) PCT No.: PCT/JP2020/021391
§ 371 (c)(1),
(2) Date: Nov. 23, 2022

(87) PCT Pub. No.: WO2021/240799
PCT Pub. Date: Dec. 2, 2021

(65) Prior Publication Data
US 2023/0200999 A1 Jun. 29, 2023

(51) Int. Cl.
*A61F 2/36* (2006.01)
*A61F 2/30* (2006.01)
*A61L 27/32* (2006.01)

(52) U.S. Cl.
CPC ............ *A61F 2/30* (2013.01); *A61F 2/30771* (2013.01); *A61F 2/3094* (2013.01); *A61F 2/367* (2013.01); *A61L 27/32* (2013.01); *A61F 2002/3006* (2013.01); *A61F 2002/30321* (2013.01); *A61F 2002/30324* (2013.01); *A61F 2002/30677* (2013.01); *A61F 2002/30784* (2013.01); *A61F 2002/30827* (2013.01); *A61F 2310/00796* (2013.01); *A61L 2300/404* (2013.01)

(58) Field of Classification Search
CPC .............. A61F 2/30; A61F 2002/30324; A61F 2002/30784; A61F 2002/30827; A61F 2/0077; A61F 2/30767
See application file for complete search history.

(56) References Cited

U.S. PATENT DOCUMENTS

| | | | | |
|---|---|---|---|---|
| 5,246,530 | A | | 9/1993 | Bugle et al. |
| 5,658,334 | A | * | 8/1997 | Caldarise .................. B29B 9/12 623/923 |
| 2005/0161120 | A1 | | 7/2005 | Inagaki |
| 2007/0116734 | A1 | * | 5/2007 | Akash ........................ A61F 2/30 264/44 |
| 2011/0008407 | A1 | | 1/2011 | Gan |
| 2013/0138223 | A1 | * | 5/2013 | Mawatari ................ A61L 27/32 623/23.61 |

(Continued)

FOREIGN PATENT DOCUMENTS

| | | | | | |
|---|---|---|---|---|---|
| JP | | 11047173 | A | * 2/1999 | .............. A61F 2/36 |
| JP | 2005000519 | A | | 1/2005 | |

(Continued)

*Primary Examiner* — Thomas C Barrett
*Assistant Examiner* — Teresa M Dudden
(74) *Attorney, Agent, or Firm* — Procopio, Cory, Hargreaves & Savitch LLP

(57) ABSTRACT

In the present disclosure, an artificial joint stem includes a base having an outer surface including a rough surface, and a coating film disposed on the rough surface of the base and containing a calcium phosphate-based material and an antimicrobial agent. The rough surface includes an exposed region exposed from the coating film.

18 Claims, 12 Drawing Sheets

(56)  References Cited

U.S. PATENT DOCUMENTS

| 2015/0056264 | A1 |   | 2/2015 | Gan |
| 2018/0200062 | A1 | * | 7/2018 | Meyenhofer ............ A61F 2/34 |
| 2018/0280571 | A1 |   | 10/2018 | Kasinath |
| 2018/0361022 | A1 |   | 12/2018 | Hotokebuchi et al. |

FOREIGN PATENT DOCUMENTS

| JP | 2011-512959 | A |   | 4/2011 |   |
| JP | 2012-040194 | A |   | 3/2012 |   |
| JP | 2018164733 | A |   | 10/2018 |   |
| WO | 1997046179 | A1 |   | 12/1997 |   |
| WO | WO-9746179 | A1 | * | 12/1997 | ............ A61F 2/367 |

* cited by examiner

101

21A

211A

10

ARTIFICIAL JOINT STEM

TECHNICAL FIELD

The present disclosure relates to an artificial joint stem.

BACKGROUND OF INVENTION

The use of a biological implant for the treatment of both bone injuries and diseases is constantly expanding with the growth of the active population and aging population. In such a situation, a known biological implant is provided with a coating from the viewpoint of antimicrobial properties, adherence to bone, and the like.

For example, Patent Document 1 describes a coating for a medical implant, in which a part of the coating contains a bone-binding agent and an antimicrobial metal agent containing silver.

CITATION LIST

Patent Literature

Patent Document 1: JP 2011-512959 T

SUMMARY

In the present disclosure, an artificial joint stem includes a base having an outer surface including a rough surface, and a coating film disposed on the rough surface of the base and containing a calcium phosphate-based material and an antimicrobial agent. The rough surface includes an exposed region exposed from the coating film.

BRIEF DESCRIPTION OF THE DRAWINGS

FIG. 3 is a cross-sectional view of A-A'.

DESCRIPTION OF EMBODIMENTS

Hereinafter, an embodiment will be described in detail. Note that, unless otherwise specified in the present specification, "A to B", which represents a numerical range, means "A or more and B or less".

1. Artificial Joint Stem

Figure 1:
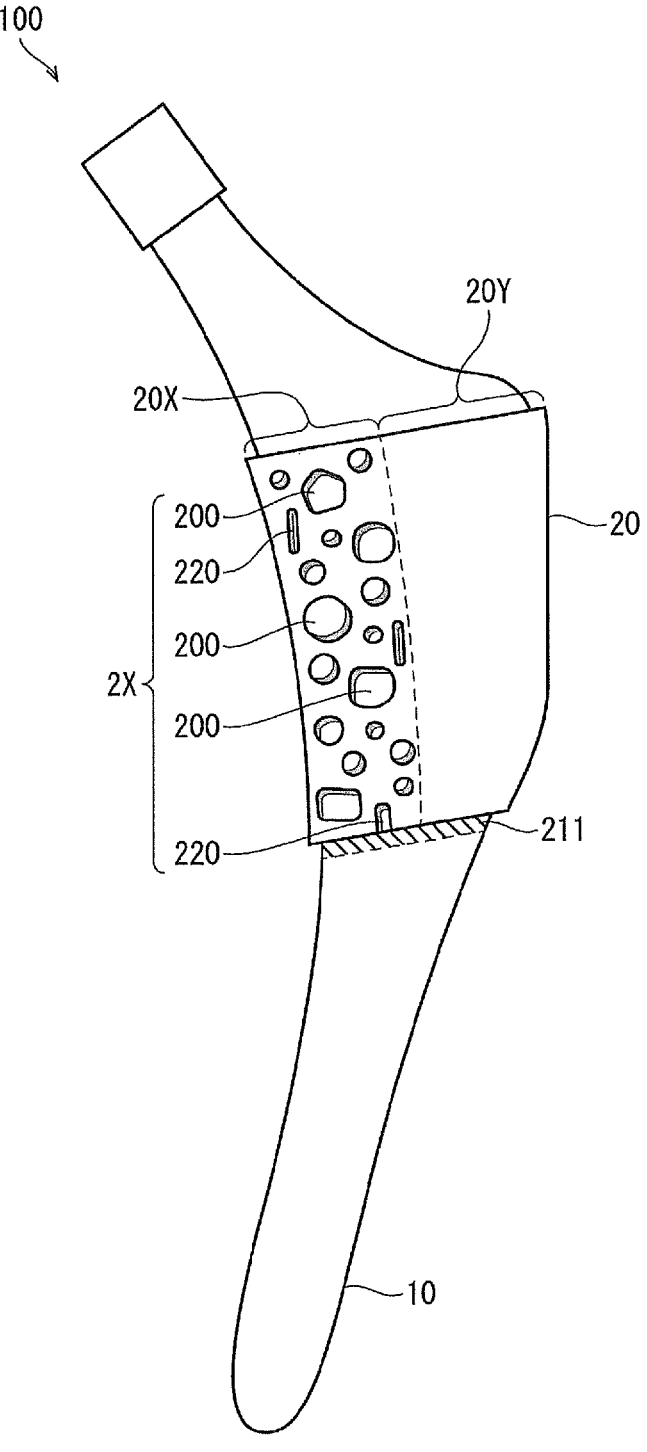
FIG. 1 is a schematic view illustrating an artificial joint stem according to an embodiment.
Figure 2:
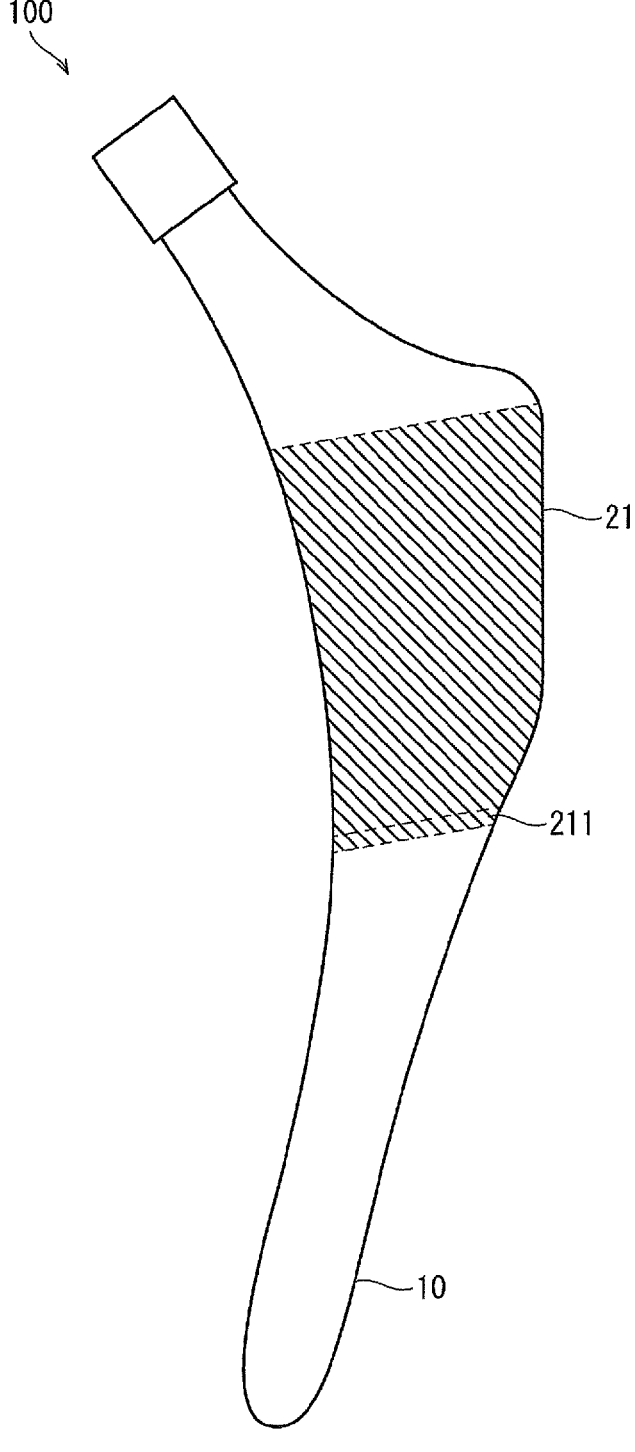
FIG. 2 is a schematic view illustrating a rough surface of an artificial joint stem according to an embodiment.

First, with reference to FIGS. 1 to 6, the configuration of an artificial joint stem 100 and an artificial joint stem 101 according to an embodiment will be described. The artificial joint stem 100 and the artificial joint stem 101 are examples of the artificial joint stem according to the present embodiment, and the artificial joint stem 100 and the artificial joint stem 101 differ in terms of a rough surface on the outer surface of the artificial joint stem and a region where a coating film is disposed on the surface. FIG. 1 is a schematic view illustrating the artificial joint stem 100, and FIG. 2 is a view illustrating a state in which a coating film 20 is removed from the artificial joint stem 100 and a rough surface 21 is visible. As illustrated in FIG. 1, the artificial joint stem 100 includes a base 10 and the coating film 20 located on the base 10. The coating film 20 includes a calcium phosphate-based material and an antimicrobial material. The calcium phosphate-based material has an effect of improving adherence to bone. The antimicrobial material is also effective in reducing bacterial adhesion and growth.

The surface of the coating film 20 includes at least one recessed portion 2X such as a hole 200 and a groove 220. In the surface of the coating film 20, a region 20X where the recessed portion 2X is disposed is smaller than another region 20Y. The recessed portion 2X includes a plurality of holes 200 disposed non-continuously with each other. At least one of the plurality of holes 200 has a polygonal planar shape at the bottom.

The coating film 20 is disposed on the rough surface 21 illustrated in FIG. 2, and a part of the rough surface 21 is exposed without being covered with the coating film 20. That is, the rough surface 21 includes an exposed region 211 exposed from the coating film 20. Since the coating film 20 is located on the rough surface 21, peeling of the coating film 20 can be reduced.

The surface roughness of the exposed region 211 is greater than that of the coating film 20.

As illustrated in FIG. 2, the exposed region 211 is smaller than a region where the coating film of the rough surface 21 is disposed. The exposed region 211 is located only on the lower end side of the coating film 20 when a proximal side of a human body using the artificial joint stem 100 is defined as an upward direction. The edge of the lower end portion of the coating film 20 is along the edge of the lower end portion of the rough surface 21.

A plurality of grooves 220 exist, and at least one groove 220 (first groove) of the plurality of grooves includes one end located in the exposed region 211. At least one groove (second groove) of the other grooves is located with both ends in the coating film 20.

Figure 5:
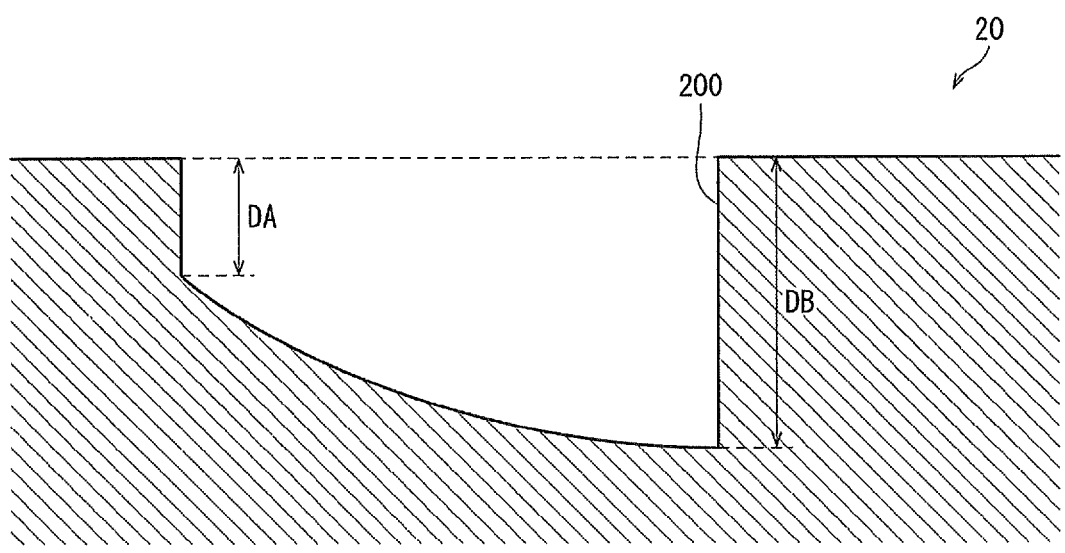
FIG. 5 is a schematic view illustrating a cross section of a hole provided on a surface of a coating film of an artificial joint stem according to an embodiment.

Next, the plurality of holes 200 will be described in detail with reference to FIG. 5. FIG. 5 is a schematic view illustrating a cross section of each hole of the plurality of holes 200.

As illustrated in FIG. 5, the depth of each hole of the plurality of holes 200 increases along one direction. In the example illustrated in FIG. 5, one depth of each hole of the plurality of holes 200 is DA, the other depth is DB, and DA<DB.

Figure 3:
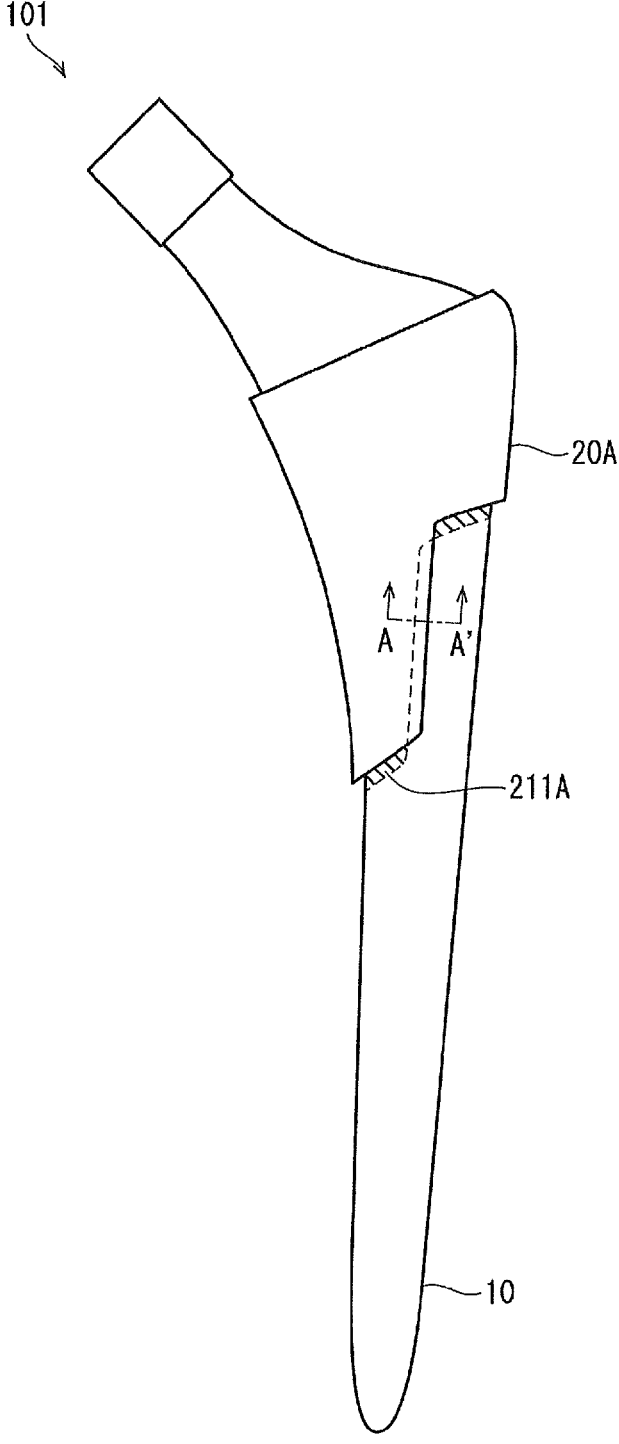
FIG. 3 is a schematic view illustrating an artificial joint stem according to an embodiment.

FIG. 3 is a schematic view illustrating the artificial joint stem 101, and FIG. 3 is a view illustrating a state where a coating film 20A is removed from the artificial joint stem 101 and a rough surface 21A is visible. Similar to the artificial joint stem 100 illustrated in FIG. 1, the artificial joint stem 101 illustrated in FIG. 3 also includes the base 10 and the coating film 20A located on the base 10. The coating film 20A includes calcium phosphate-based material and antimicrobial material.

The artificial joint stem 101 differs from the artificial joint stem 100 in terms of the shape of the coating film 20 and the rough surface 21. As illustrated in FIG. 3, the vertical length of the coating film 20A in the artificial joint stem 101 varies depending on the location.

Figure 4:
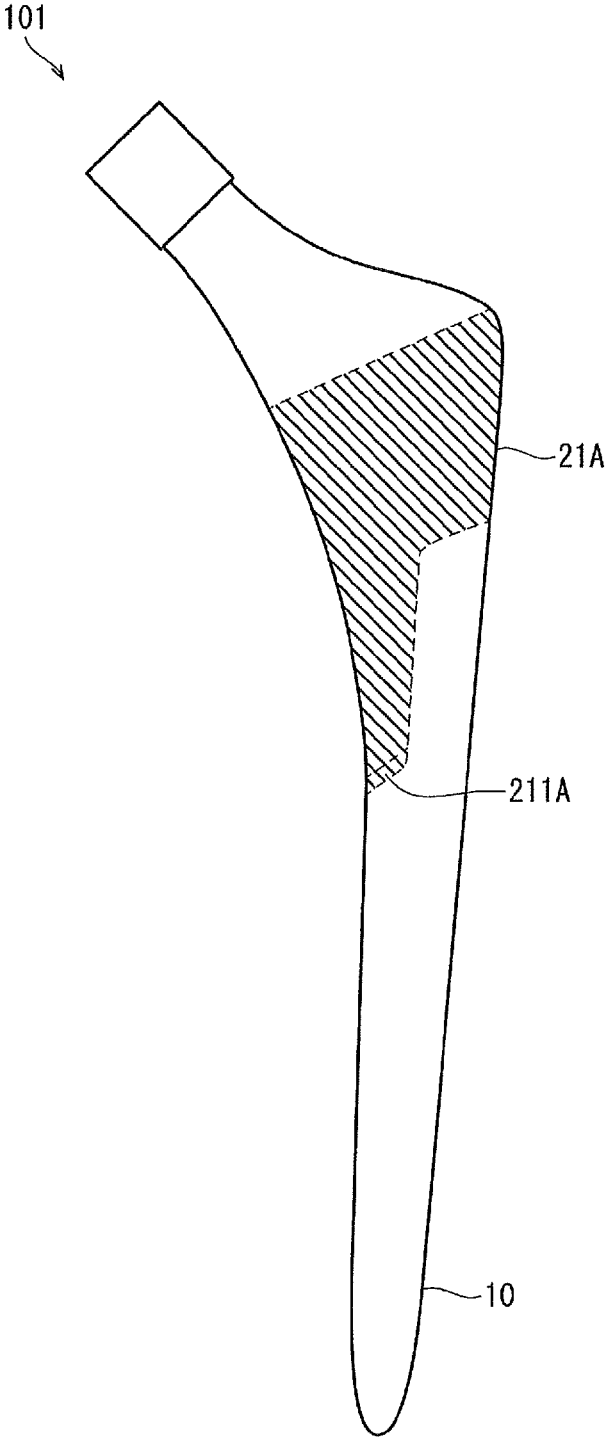
FIG. 4 is a schematic view illustrating a rough surface of an artificial joint stem according to an embodiment.

As illustrated in FIGS. 3 and 4, the edge of the coating film 20A is non-parallel to the edge of the rough surface 21A.

Figure 6:
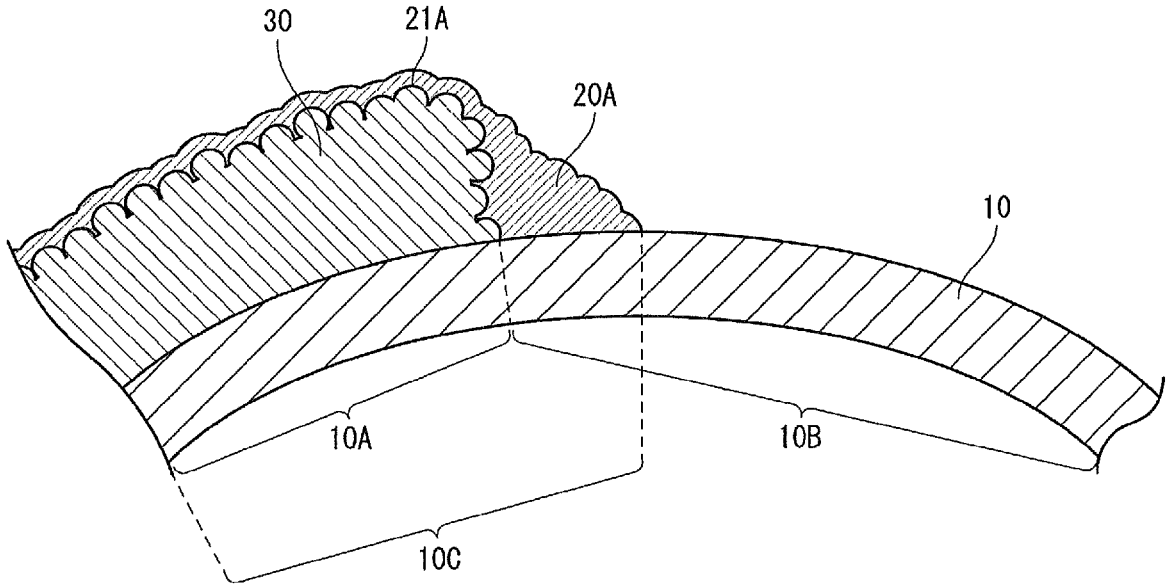
FIG. 6 is a view illustrating a cross section of an artificial joint stem according to an embodiment.

FIG. 6 is an enlarged view of the surface layer of the cross section A-A' of FIG. 3. The base 10 includes a region 10A corresponding to the rough surface 21A and another region 10B, and the coating film 20A is formed so as to straddle the region 10A and the region 10B. That is, the coating film 20A is disposed so as to cover two kinds of surfaces together at the boundary portion between the two kinds of surfaces adjacent to each other. In the region 10B, regions not covered with the coating film 20A are exposed from the coating film 20A.

As described above, the coating film 20A includes a coating film region 10C, which is located to straddle the region 10A and the region 10B that is an outer surface different from the region 10A. The coating film region 10C is located on the lower end side of the base 10. A surface roughness of the outer surface where the coating film region 10C is located is greater than that of the region 10B exposed from the coating film region 10C.

In the artificial joint stem 100 and the artificial joint stein 101, for example, the arithmetic mean roughness Sa (ISO 25178) is used as an index of the surface roughness. The surface roughness (Sa) of the coating film 20 (20 A) may be set to, for example, from 10 to 80 μm, from 20 to 80 μm, or from 30 to 70 μm. The surface roughness (Sa) of the base 10 may be only required to be set to, for example, less than 1.0 μm.

The surface roughness Sa can be determined from the measurement result of the whole region (e.g., the region corresponding to the rough surface 21, or the rough surface 21A). The surface roughness of the coating film 20 (20A) or the surface roughness of the base 10 is only required to be measured, for example, by a stylus method or an optical method. The surface roughness is only required to be measured in accordance with "ISO 25178", for example. Note that methods for measuring surface roughness are not limited to the above-described methods.

Here, in the related art, there has been room for improvement in the artificial joint stem from the viewpoint of achieving control of both antimicrobial properties and adherence to bone. That is, for example, in the case where the entire surface of an artificial joint stem is covered with a coating containing a bone-binding agent and an antimicrobial metal agent, the control of the adherence between the artificial joint stem and a bone is difficult. In this case, removal of the artificial joint stem may become difficult when removal of the artificial joint stem is required after surgery. For example, a portion of the artificial joint stem 100 (101) embedded in the bone may be excessively adhered to the bone via the coating.

In the present disclosure, the artificial joint stem 101 includes the coating film 20A that straddles regions 10A and 10B, and the surface roughness of the coating film 20A in the region 10A is greater than that in the region 10B. Thus, the adherence to bone and the antimicrobial properties can be sufficiently achieved. On the other hand, the region 10B is exposed from the coating film 20A and has a smaller surface roughness than the region 10A. Thus, excessive adhesion to the bone can be reduced. As described above, according to the artificial joint stem 101, both antimicrobial properties and adherence to bone can be controlled.

As the base 10, a metal, ceramic or plastic may be used. Examples of the metal include stainless steel alloy, cobalt-chromium alloy, titanium, and titanium alloy. The titanium alloy can be made by adding at least one selected from the group consisting of aluminum, tin, zirconium, molybdenum, nickel, palladium, tantalum, niobium, vanadium, and platinum to titanium. Examples of the ceramic include alumina, zirconia and alumina-zirconia composite ceramic. Examples of the plastic include polyethylene, fluorine-based resin, epoxy resin, polyetheretherketone (PEEK) resin, and bakelite. Note that, in the present embodiment, the base 10 is made of a titanium alloy.

The shape of the base 10 may be substantially rod-shaped, for example, but may be appropriately changed according to the shape of the artificial joint to be applied.

The artificial joint stem 101 may further include a layer member 30. The layer member 30 may be disposed on the region 10A. Thus, as illustrated in FIG. 6, the region 10A is higher than the region where the layer member 30 is not provided. Accordingly, when the artificial joint stem 101 is embedded in the bone, the region 10A can mainly be brought into contact with the bone. As used herein, "layer member" means a member different from the coating film 20 that is layered on the base 10. For example, the surface of the layer member 30 may be a rough surface. Thus, the region primarily in contact with the bone can have a rough surface. The layer member 30 may be formed by a thermal spraying method as described below. Alternatively, the layer member 30 may be formed as a porous structure.

Note that the lower limit of the height of the layer member 30 may be only required to be set to, for example, 100 μm or more, and may be set to 300 μm or more. The upper limit may be only required to be set to, for example, 1000 μm or less, and may be set to 700 μm or less. The surface roughness of the layer member 30 may be set to, for example, 10 to 80 μm, 20 to 80 μm, or 30 to 70 μm.

Thus, the thickness of the layer member 30 is greater than the thickness of the coating film 20A.

The base 10 may be formed in such a manner that the region 10A can mainly be brought into contact with the bone without providing the layer member 30. For example, the region 10A may have a raised shape with respect to the region 10B.

As the material of the layer member 30, the material exemplified as the material of the base 10 can be used. For example, the layer member 30 may be made of a metal. The material of the layer member 30 and the material of the base 10 may be the same or different. Thus, sufficient strength can be secured. Note that in the present embodiment, the layer member 30 is made of a titanium alloy.

The layer member 30 may have an edge lower in height than the interior of the layer member 30. As used herein, the "interior of the layer member" means the interior of the layer member 30 in the planar direction. Thus, the concentration of stress on the edge of the layer member 30 can be reduced.

The coating film 20 includes a calcium phosphate-based material and an antimicrobial material. Examples of the calcium phosphate-based material include one or more types of mixtures selected from the group consisting of hydroxy-apatite, α-tertiary calcium phosphate, β-tertiary calcium phosphate, quaternary calcium phosphate, octacalcium phosphate, and calcium phosphate-based glass. As the anti-microbial material, a natural antimicrobial agent, an organic antimicrobial agent, or an inorganic antimicrobial agent can be used. For example, hinokitiol can be used as a natural antimicrobial agent, benzalkonium chloride can be used as an organic antimicrobial agent, and a metal can be used as an inorganic antimicrobial agent. Examples of the metal include silver, copper, and zinc. In addition to the calcium phosphate-based material and the antimicrobial material, the coating film 20 may contain a glass ceramic, and may further contain an antimicrobial agent such as penicillin and van-comycin.

The concentration of the antimicrobial material in the coating film 20 may be, for example, from 0.05 wt % to 3.00 wt %, from 0.05 wt % to 2.50 wt %, from 0.05 wt % to 1.00 wt %, or from 0.1 wt % to 1.00 wt %. When the concen-tration of the antimicrobial material is 0.05 wt % or more, sufficient antimicrobial properties can be achieved. When the concentration of the antimicrobial material is 3.00 wt % or less, the impact on living tissue can be reduced.

There may be a concentration gradient of antimicrobial material in the coating film 20. For example, the concen-tration of the antimicrobial material contained in an upper end portion of the coating film 20 may be greater than the concentration of the antimicrobial material contained in a lower end portion of the coating film. Thus, invasion of bacteria from the upper end portion side of the coating film 20 can be more effectively reduced. The antimicrobial material may be contained only at the upper end portion of the coating film 20.

On the base 10, there may be one or more boundary lines defined by the presence or absence of the coating film 20. Of the one or more boundary lines, at least one boundary line has a circumferential length around the base 10 that may be larger than a circumferential length of a part of the base 10 located above and below the at least one boundary line. For example, a portion where the at least one boundary line exists may be raised in a node shape on the base 10.

The coating film 20 may be disposed on the layer member 30. As described above, the layer member 30 may be mainly in contact with the bone. The coating film 20 is disposed on the layer member 30, which can further improve the adher-ence to bone and the antimicrobial properties.

The height of the layer member 30 may be greater than the thickness of the coating film 20. Thus, since the region where the layer member 30 is formed is higher than the region where only the coating film 20 is formed, the region where the layer member 30 is formed can mainly be brought into contact with the bone. The thickness of the coating film 20 may be only required to be set to, for example, less than 100 μm, and may be set to less than 50 μm. The coating film 20 may be only required to be, for example, set to be 5 μm or more.

The region 10B is exposed from the coating film 20A. A region where the coating film 20A is disposed and a region exposed from the coating film 20A can be distinguished from each other by an elemental analysis of the surface of each region. The method of elemental analysis can be performed, for example, by mapping the surface elements with an energy dispersive X-ray spectrometry (EDX) appa-ratus, which is an accessory for a general scanning electron microscope (SEM). Surface analysis methods such as X-ray photoelectron spectroscopy, Auger electron spectroscopy, and secondary ion mass spectrometry may also be used. The element may be confirmed by chemical analysis of a sample obtained by mechanically scraping off the surface of each region. For example, on the surface of the region 10A where the coating film 20A is disposed, phosphorus, calcium, antimicrobial components, or the like are detected. From the surface of the region 10B, elements constituting the base 10 are detected, and phosphorus, calcium, antimicrobial com-ponents, or the like are not detected, or are detected at a noise level or lower.

The base 10 as described above may include a body portion and a neck portion connected to the upper end portion of the body portion. The body portion may be embedded in a femur portion. The neck portion is exposed from the femur, provided with a bone head, and may be placed in an acetabular cup that constitutes a pair with the artificial joint stem.

The body portion has a lower portion having a center axis extending in the vertical direction, and an upper portion having a shape including a bend extending continuously in the vertical direction from the lower portion and curved such that the center is separated from the center axis as advancing upward. Note that, for the vertical direction of the base 10, the upward direction corresponds to the proximal direction and the downward direction corresponds to the distal direc-tion of a human body. The upper portion includes an upper end face disposed away from the center axis, and the neck portion is connected to the upper end face. The neck portion is smaller in width than the body portion (upper end face). In other words, the neck portion can be also referred to as a protruding portion protruding from the body portion in an oblique direction inclined from the center axis.

The base 10 may further include a collar provided at a connecting portion between the body portion and the neck portion. The collar is a protruding portion protruding from the connecting portion toward the planar direction of the upper end face. The collar can suppress the body portion from getting too far into the femur during artificial joint stem surgery.

Figure 9:
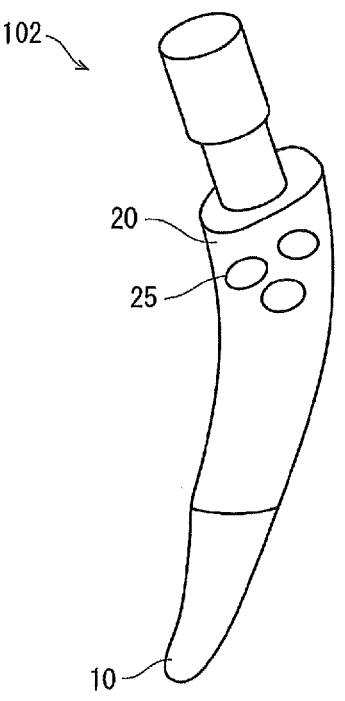
FIG. 9 is a schematic view illustrating an artificial joint stein according to an embodiment.

In the present disclosure, the artificial joint stem also includes an artificial joint stem 102 illustrated in FIG. 9. For example, a recessed portion 25 including an opening in the surface of the coating film 20 may be provided. The opening area of the recessed portion 25 located on the upper end portion side of the coating film 20 may be greater than the opening area of the recessed portion 25 located on the lower end portion side of the coating film 20. The recessed portion 25 may be provided only at the upper end portion of the coating film 20.

Figure 10:
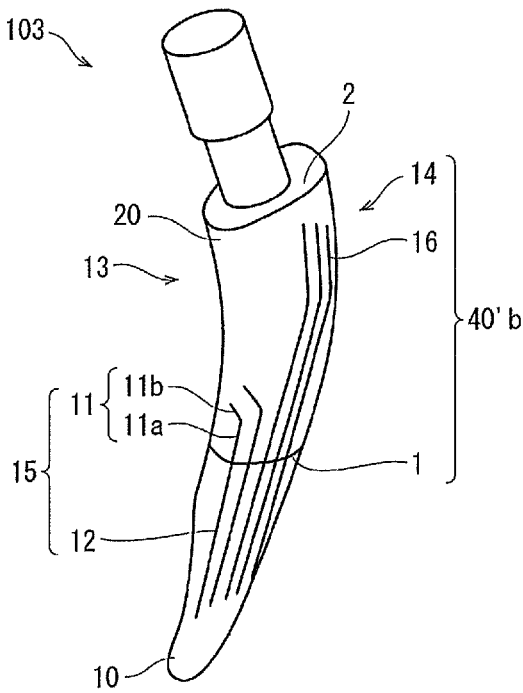
FIG. 10 is a schematic view illustrating an artificial joint stem according to an embodiment.

In the present disclosure, the artificial joint stem also includes an artificial joint stem 103 illustrated in FIG. 10. For example, the base 10 may include a groove. The groove may straddle the region where the coating film 20 is dis-posed and the region exposed from the coating film 20. The groove may extend to the upper end portion of the coating film 20. The surface roughness in the groove located on the rough surface may be smaller than that of the base 10 located on the rough surface.

The base 10 may include an inner side portion 13 that curves concavely and an outer side portion 14 that curves convexly. Here, the groove extends in the vertical direction, and the upper end of the groove may be located at the bend. At a contraction portion 40'*b*, the groove may be bent to either the inner side portion 13 or the outer side portion 14. For example, the groove may be bent at the contraction portion 40'*b* to the inner side portion 13. The depth of the lower end portion of the groove may be smaller than that of the upper end portion of the groove. The width of the lower end portion of the groove may be smaller than the width of the upper end portion of the groove. One end of the groove may be exposed from the coating film 20, and the other end may be located at the contraction portion 40'*b*.

The groove located in the region where the coating film 20 is disposed is defined as a first groove 11, and the groove located in the region where the surface of the base 10 is exposed from the coating film 20 is defined as a second groove 12. The first groove 11 may or may not be connected to the second groove 12. That is, the first groove 11 and the second groove 12 may be formed as a single continuous groove. The upper end portion of the first groove 11 may be bent to the inner side portion 13. In other words, the first groove 11 may include a first portion 11*a* extending in the vertical direction of the base 10 and a second portion 1*b* connected to the first portion 11*a* and having a component along the width direction of the base 10. The depth of the second groove 12 may be smaller than the depth of the first groove 11.

The base 10 may include a plurality of grooves. The base 10 may also include a first groove set 15 and a second groove set 16. The first groove set 15 includes the first groove 11 and the second groove 12 connected to each other. The second groove set 16 includes the first groove 11 and the second groove 12 connected to each other, and the first groove 11 extends to the upper end portion of the coating film 20 further than the first groove set 15.

In addition, the base 10 may include a plurality of first groove sets 15. The plurality of the first groove sets 15 may be arranged in the width direction of the base 10. Of the plurality of the first groove sets 15, the first groove set 15 located on the outer side portion 14 side may be located above the first groove set 15 located on the inner side portion 13 side.

Figure 11:
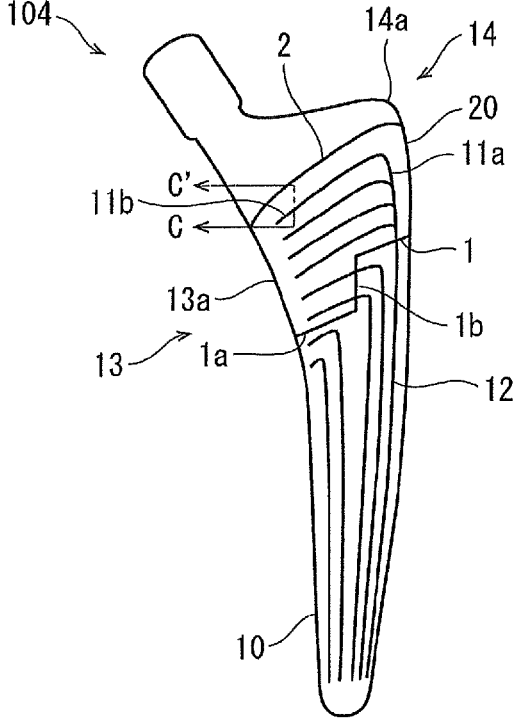
FIG. 11 is a schematic view illustrating an artificial joint stem according to an embodiment.
Figure 12:
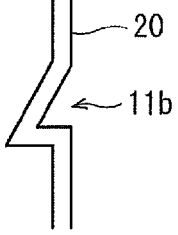
FIG. 12 is a schematic view illustrating a cross section of an artificial joint stem according to an embodiment.

In the present disclosure, the artificial joint stem also includes an artificial joint stem 104 illustrated in FIG. 11. For example, the base 10 may include a plurality of grooves, and a groove located on the upper portion of the base 10 may be wider than a groove located on the lower portion of the base 10. The grooves may have a component along the width direction of the base 10. FIG. 12 illustrates a C-C' cross section of FIG. 11. As illustrated in FIG. 12, the groove along the width direction of the base 10 may be shallower upward.

The edge of the lower end (first boundary line 1) of the coating film 20 may intersect the linear portion of the groove. Here, the first boundary line 1 may diagonally intersect the linear portion of the groove. That is, the first boundary line 1 need not be orthogonal to the linear portion of the groove.

The first boundary line 1 may include a first portion 1*a* extending in a direction intersecting the groove and a second portion 1*b* extending in a direction along the groove. The second portion 1*b* may be separated from the groove. That is, the second portion 1*b* need not be in contact with the groove. The same is true for the edge of the upper end (second boundary line 2) of the coating film 20.

The first groove 11 and the second groove 12 are connected. The first groove 11 may include the first portion 11*a* extending in the vertical direction of the base 10 and the second portion 11*b* connected to the first portion 11*a* and having a component along the width direction of the base 10. As illustrated in FIG. 11, the second boundary line 2 may extend in a direction along the second portion 11*b* of a first groove 11.

As illustrated in FIG. 11, the second boundary line 2 may be disposed so as to incline upward from the inner side portion 13 toward the outer side portion 14. As illustrated in FIG. 11, the first boundary line 1 may be located below an apex 13*a* of the recessed portion at the inner side portion 13. A first boundary line 2 may be located below an apex 14*a* of the protruding portion at the outer side portion 14. Alternatively, the first boundary line 1 may be located above the apex 14*a* of the protruding portion at the outer side portion 14.

Figure 13:
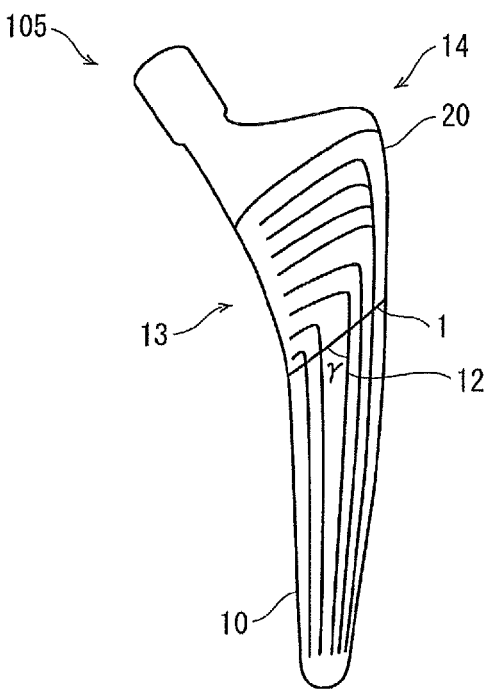
FIG. 13 is a schematic view illustrating an artificial joint stem according to an embodiment.

In the present disclosure, the artificial joint stem also includes an artificial joint stem 105 illustrated in FIG. 13. For example, each of the one or more boundary lines defined by the presence or absence of the coating film 20 may intersect the groove with an acute angle. In FIG. 13, an angler on the inner side portion 13 side of the angles formed by the first boundary line 1 and the second groove 12 is a sharp angle.

Figure 14:
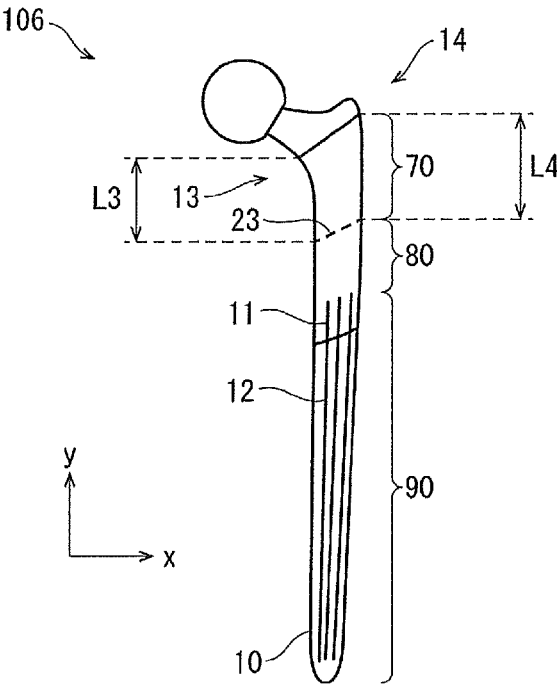
FIG. 14 is a schematic view illustrating an artificial joint stem according to an embodiment.
Figure 15:
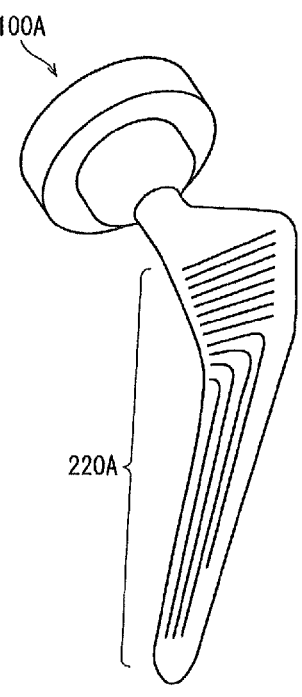
FIG. 15 is a schematic view illustrating an artificial joint stem according to an embodiment.
Figure 16:
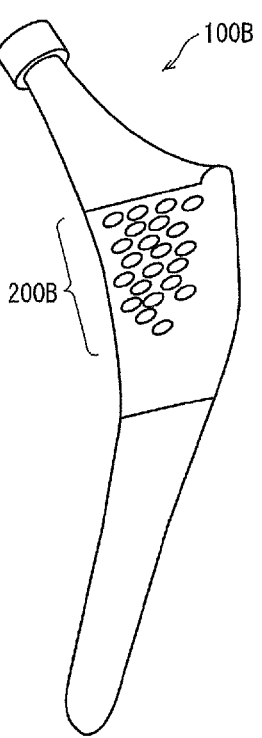
FIG. 16 is a schematic view illustrating an artificial joint stem according to an embodiment.

In the present disclosure, the artificial joint stem also includes an artificial joint stem 106 illustrated in FIG. 14. For example, the base 10 includes, from top to bottom, a rough surface region 70, a non-rough-surface region 80, and a groove region 90. A rough surface is disposed in the rough-surface region 70. The non-rough-surface region 80 is a region without a rough surface. The grooves are disposed in the groove region 90. For example, the rough-surface region 70 may be a region in which rough surfaces are disposed but no grooves are disposed. The non-rough-surface region 80 may be a region in which neither a rough surface nor a groove is disposed. The groove region 90 may be a region in which a rough surface is not disposed but a groove is disposed. The coating film 20 may cover at least one selected from the group consisting of the rough-surface region 70, the non-rough-surface region 80 and the groove region 90. The area of the rough-surface region 70 may be smaller than that of the non-rough-surface region 80. In the width direction of the base 10, the length of the rough-surface region 70 may be greater than the length of the non-rough-surface region 80. One or more boundary lines 23 between the rough-surface region 70 and the non-rough-surface region 80 may be inclined upward from the inner side portion 13 toward the outer side portion 14. A length L3 on the inner side portion 13 side of the rough-surface region 70 may be less than the length L4 on the outer side portion 14 side of the rough-surface region 70. Here, the length L3 represents a difference in Y coordinate between a point where the Y coordinate is the maximum and a point where the Y coordinate is the minimum, on the inner side portion 13 side of the rough-surface region 70. A length L4 represents a difference in the Y coordinate between a point where the Y coordinate is maximum and a point where the Y coordinate is minimum, on the outer side portion 14 side of the rough-surface region 70.

Figure 17:
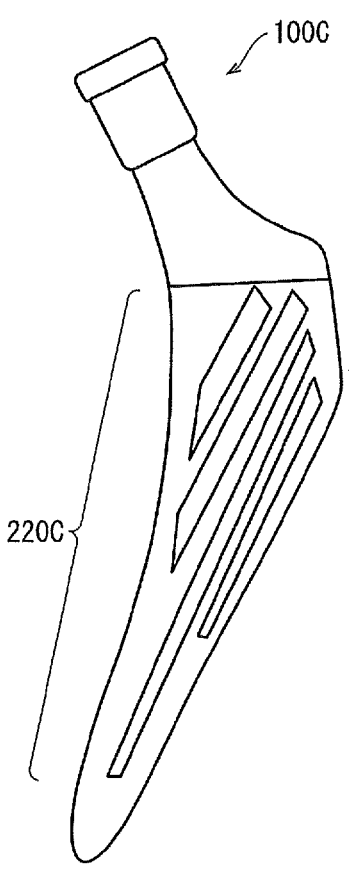
FIG. 17 is a schematic view illustrating an artificial joint stem according to an embodiment.
Figure 18:
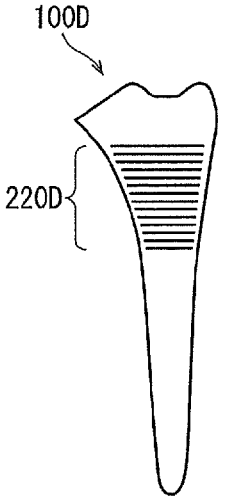
FIG. 18 is a schematic view illustrating an artificial joint stem according to an embodiment.
Figure 19:
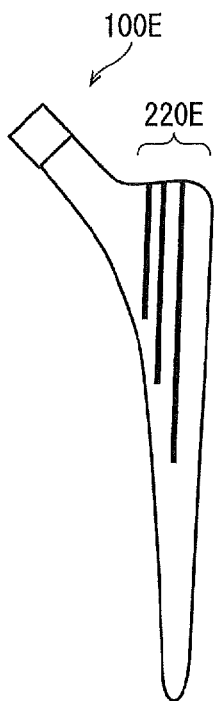
FIG. 19 is a schematic view illustrating an artificial joint stem according to an embodiment.
Figure 20:
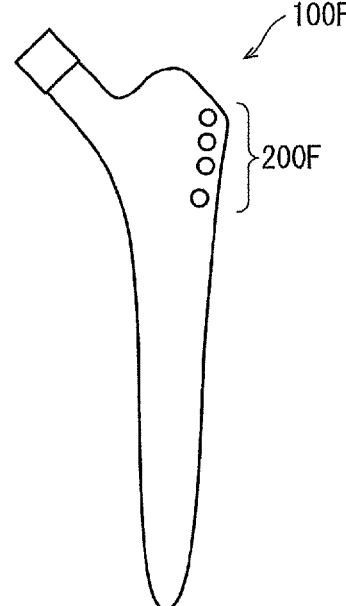
FIG. 20 is a schematic view illustrating an artificial joint stem according to an embodiment.

In the present disclosure, the artificial joint stem also includes artificial joint stems 100A to 100F illustrated in FIGS. 15 to 20. For example, a groove 220A may be provided as in the artificial joint stem 100A, a hole 200B may be provided as in the artificial joint stem 100B, a groove 220C may be provided as in the artificial joint stem 100C, a groove 220D may be provided as the artificial joint stem 100D, a groove 220E may be provided as in the artificial joint stem 100E, or a hole 200F may be provided as in the artificial joint stem 100F. In the above example, the exposed regions are provided at the upper and lower ends of the coating film 20, but as illustrated in FIG. 17, the exposed regions may be located only on the upper side of the coating film 20.

2. Method of Manufacturing Artificial Joint Stem

In an embodiment, a method of manufacturing an artificial joint stem includes a preparation step, a roughening step, and a coating film forming step. In the preparation step, the base 10 having a surface that includes a first region, a second region, and a roughening region overlapping at least a part of the first region is prepared. After the base 10 is prepared, the roughening step is performed where a rough surface is formed on the roughening region of the base 10 that has been prepared. The coating film forming step is a step of forming the coating film 20 containing a calcium phosphate-based material and an antimicrobial material on the first region of the base 10. Note that at least a part of the first region and a part of the roughened region overlap. This will form the coating film 20 on the rough surface, and a part of the rough surface will be exposed from the coating film 20.

In the preparation step, the base 10 can be prepared by molding the metal material into a desired shape by using a metal mold, or an additive manufacturing method, or the like. Note that since the second region is located so as to sandwich the first region vertically in the base 10, the first boundary line and the second boundary line can be formed after the coating film 20 is formed. The shapes of the first boundary line and the second boundary line of the coating film can be adjusted according to the shape of the first region.

In the roughening step, a rough surface can be formed by at least one selected from the group consisting of a thermal spraying method, an additive manufacturing method, a chemical etching method and a blasting method. Compared with the blasting method, the thermal spraying method, the additive manufacturing method or the chemical etching method can increase the surface roughness. As the thermal spraying material and the additive manufacturing material, the material exemplified as the material for the base 10 can be used. The above-described layered structure may be formed by the thermal spraying or the additive manufacturing. Examples of the chemical etching method include alkali treatment. Examples of the blasting method include sandblasting. Note that the rough surface can be formed before forming the coating film 20.

A first protective material may be used to form a rough surface only in a desired region. In this case, before the roughening step, a step may be further provided in which in order not to form a rough surface on other than the roughening region, while exposing the roughening region, the first protective material is disposed so as to protect the other region. A part of the roughening region overlaps with a part of the first region. That is, the first protective material may be only required to be disposed to protect a part of the first region and the second region. Note that the manufacturing method may include a step of removing the first protective material after the roughening step and before the coating film forming step.

For example, a masking tape or a screen may be used as the first protective material. Alternatively, a jig covering the base 10 may be used as the first protective material. Examples of the first protective material include metals, glasses, resins, and composite materials thereof. Note that the first protective material may or may not be in contact with the base 10. When a jig covering the base 10 is used as the first protective material, the shape of the jig is not particularly limited, but may be, for example, tubular. The cross section of the tubular jig may be polygonal or circular.

When a screen is to be placed, a rough surface can be formed in a specific region by placing the screen in a predetermined position. When a jig is to be used, a rough surface can be formed in a specific region by placing the jig in a predetermined position. In this case, for example, the rough surface can be selectively formed only in a desired region by adjusting the positional relationship between the screen and a discharge nozzle for discharging the thermal spraying material, the additive manufacturing material, the chemical etching material, the blasting material, or the coating material. In this case, a tip of the discharge nozzle is only required to be disposed, for example, in a straight line with the surface of the desired region without being separated by the screen. Hereinafter, a thermal spraying material, an additive manufacturing material, a chemical etching material, a blasting material, or a coating material discharged from the discharge nozzle is also referred to as a discharge material. Without being limited to the above, the rough surface may be formed while the base 10, the screen, and the discharge nozzle are fixed, or the rough surface may be formed while moving at least one selected from the group consisting of the aforementioned. The angle of the discharge nozzle may be fixed or the rough surface may be formed while changing the angle. Note that similarly to the coating film 20, a rough surface may be formed only in a desired region without using a protective material.

Note that the rough surface can be formed only in a desired region without using a protective material. For example, the rough surface can be selectively formed only in a desired region by adjusting the shape, angle degree, or position, of the discharge nozzle for discharging the discharge material. For example, the discharge material may be discharged with the discharge nozzle located above the surface of the desired region. In this case, the rough surface may be formed by fixing the base 10 and moving the position and angle of the discharge nozzle, or the coating film 20 may be formed by fixing the discharge nozzle and moving the position and angle of the base 10. The discharge nozzle may be moved at a constant speed or at a variable speed. The discharge direction of the discharge material may be an angle of 90° or an angle of less than 90° with the vector extending from the tip of the discharge nozzle toward the base 10 or the surface of the rough surface, which are located at the shortest distance from the tip of the discharge nozzle.

The coating film 20 can be formed by: a thermal spraying method such as flame spraying, high-speed flame spraying, and plasma spraying; a physical vapor deposition method or chemical vapor deposition method such as sputtering, ion plating, ion beam deposition, and an ion mixing method; or a wet coating method such as a sol-gel method. The coating film 20 may be formed to cover at least a part of the embedded portion.

A second protective material may be used to form the coating film 20 only in the first region. In this case, the coating film forming step may further include a step of disposing the first protective material so as to protect the second region while exposing the first region so that the coating film is not formed in the second region. For example, a masking tape or a screen may be used as the second protective material. Alternatively, a jig covering the base 10 may be used as the second protective material. Examples of the second protective material include metals, glasses, resins, and composite materials thereof. Note that the second protective material may or may not be in contact with the base 10. When, for example, a masking tape is used as the first protective material, the second protective material may be disposed on the second region. When a jig covering the base 10 is used, the shape of the jig is not particularly limited, but may be, for example, tubular. The cross section of the tubular jig may be polygonal or circular. Note that a step of removing the second protective material may be provided after the coating film forming step.

When a screen is to be disposed, the coating film 20 can be formed in a specific region by placing the screen in a predetermined location. When a jig is used, the coating film 20 can be formed in a specific region by placing the jig in a predetermined location. In this case, for example, the coating film 20 can be selectively formed only in a desired region by adjusting the positional relationship between the screen and a discharge nozzle configured to discharge the thermal spraying material, the additive manufacturing material, the chemical etching material, the blasting material, or the coating material. In this case, a tip of the discharge nozzle is only required to be disposed, for example, in a straight line with the surface of the desired region without being separated by the screen. Hereinafter, a thermal spraying material, an additive manufacturing material, a chemical etching material, a blasting material, or a coating material discharged from the discharge nozzle is also referred to as a discharge material. Without being limited to the above, the coating film 20 may be formed while the base 10, the screen, and the discharge nozzle are fixed, or the coating film 20 may be formed while moving at least one selected from the group consisting of the aforementioned. The angle of the discharge nozzle may be fixed or the coating film 20 may be formed while changing the angle.

Note that the coating film 20 can be formed only in a desired region without using a protective material. For example, the coating film 20 can be selectively formed only in a desired region by adjusting the shape, angle degree, or position, of the discharge nozzle configured to discharge the discharge material. For example, the discharge material may be discharged with the discharge nozzle located above the surface of the desired region. In this case, the coating film 20 may be formed by fixing the base 10 and moving the position and angle of the discharge nozzle, or the coating film 20 may be formed by fixing the discharge nozzle and moving the position and angle of the base 10. The discharge nozzle may be moved at a constant speed or at a variable speed. The discharge direction of the discharge material may be an angle of 90° or an angle of less than 90° with the vector extending from the tip of the discharge nozzle toward the base 10 or the surface of the rough surface, which are located at the shortest distance from the tip of the discharge nozzle.

For example, in the roughening step, while exposing a region to be roughened to the base 10, a protective material may be disposed to protect other regions, thereby forming a rough surface on the exposed region. In the present disclosure, the manufacturing method may further include a step of removing the protective material after the roughening step and before the coating film forming step. After the protective material is removed, a step of scraping off the edge of the rough surface, for example, the edge of the layer member 30, may be performed. Thus, the concentration of stress at the edge of the layer member 30 can be avoided, and irritation to the biotissue can be reduced.

In an embodiment, the method of manufacturing the artificial joint stem may further include a recessed portion forming step before the coating film forming step. In the recessed portion forming step, the at least one recessed portion 2X can be formed on the surface of the base 10 by, for example, at least one selected from the group consisting of a cutting method, a rolling processing method, and a pressing method. After the recessed portion 2X is formed on the surface of the base 10 by the recessed portion forming step, a coating film may be formed on the surface of the base 10 including the inner surface of the at least one recessed portion 2X by the coating film forming step.

Figure 8:
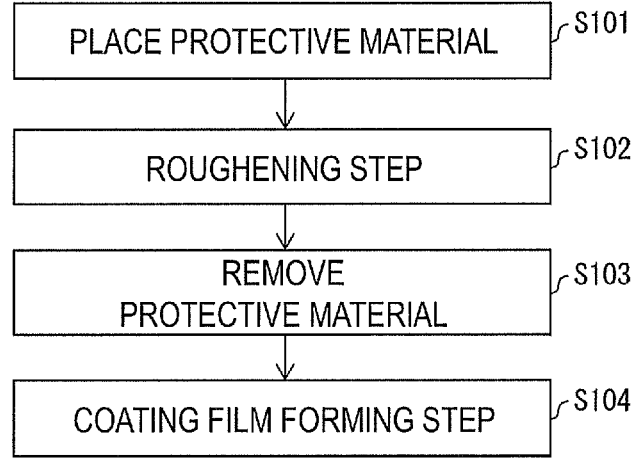
FIG. 8 is a flowchart illustrating a method of manufacturing an artificial joint stem according to an embodiment.

In summary, each step can be performed in the order illustrated in FIG. 8, for example. FIG. 8 is a flowchart illustrating a method of manufacturing an artificial joint stem according to an embodiment. First, the protective material is disposed (S101), and after a roughening step is performed (S102), the protective material can be removed (S103). Next, the coating film forming step can be performed (S104).

In the present disclosure, the manufacturing method may or may not include a cleaning step between each step. For example, in the present disclosure, the manufacturing method includes a step of cleaning the base 10, or the base 10 and the layer member 30 after the roughening step. The cleaning method is not particularly limited, but may be, for example, a method of immersing in a liquid such as water or an organic solvent such as alcohol, or a method of showering using the liquid. Alternatively, a method of blowing a gas such as air, nitrogen or argon may be employed. Thus, excess thermal spraying material and the like generated by the roughening step can be removed.

Note that the roughening step may include, in order, a first roughening step of forming a first rough surface by a thermal spraying method and a second roughening step of forming a second rough surface by a chemical etching method or a blasting method. Herein, a region where the first rough surface is formed by thermal spraying method is referred to as a first roughening region, a region where the second rough surface is formed by chemical etching method or blasting method is referred to as a second roughening region, and a region where no rough surface is formed is referred to as a non-roughening region.

In the first roughening step, a protective material may be disposed on the base 10 to protect the second roughening region and the non-roughening region while exposing the first roughening region, thereby forming the first rough surface on the exposed first roughening region. In the present disclosure, the manufacturing method may further include a step of removing the protective material after the first roughening step and before the second roughening step. In the second roughening step, a protective material may be disposed on the base 10 to protect the non-roughening region while exposing the second roughening region, thereby forming the second rough surface on the exposed second roughening region. The second roughening step may be performed such that the surface of the second rough surface formed in the second roughening step has a surface roughness smaller than that of the first rough surface in the first roughening region. In the present disclosure, the manufacturing method may include a step of removing the protective material after the second roughening step and before the coating film forming step. For example, a masking tape may be used as the protective material. In the present disclosure, the manufacturing method may further include a step of attaching a masking tape to a non-roughening region while exposing a first roughening region 1 and a second roughening region 2 before the second roughening step. As the protective material, a material having lower thermal resistance than the protective material used on the first roughening step described above may be used. For example, a material that does not melt or thermally decompose at room temperature may be used as the protective material. Specifically, a resin may be used as the protective material.

In the second roughening step, the non-roughening region may or may not be covered with a protective material. The first roughening region and the non-roughening region may be protected, and only the second roughening region may be processed by at least one selected from the group consisting of chemical etching method and blasting method. Alternatively, a protective material may be disposed so as to expose the first roughening region. Then, the rough surface of the exposed first roughening region, and the second roughening region, may be processed by a chemical etching method and/or a blasting method. Thus, an excess thermal spraying material or the like remaining on the rough surface of the first roughening region can be removed, and a rough surface can be also formed on the second roughening region.

3. Use of Artificial Joint Stem

Although the artificial joint stem 100 (101) has a shape mainly assuming a stem for an artificial hip joint, artificial joints to which the artificial joint stem according to the present disclosure is applied, are not limited to artificial hip joints. Examples of the artificial joint include an artificial hip joint, an artificial knee joint, an artificial ankle joint, an artificial shoulder joint, an artificial elbow joint and an artificial finger joint.

Figure 7:
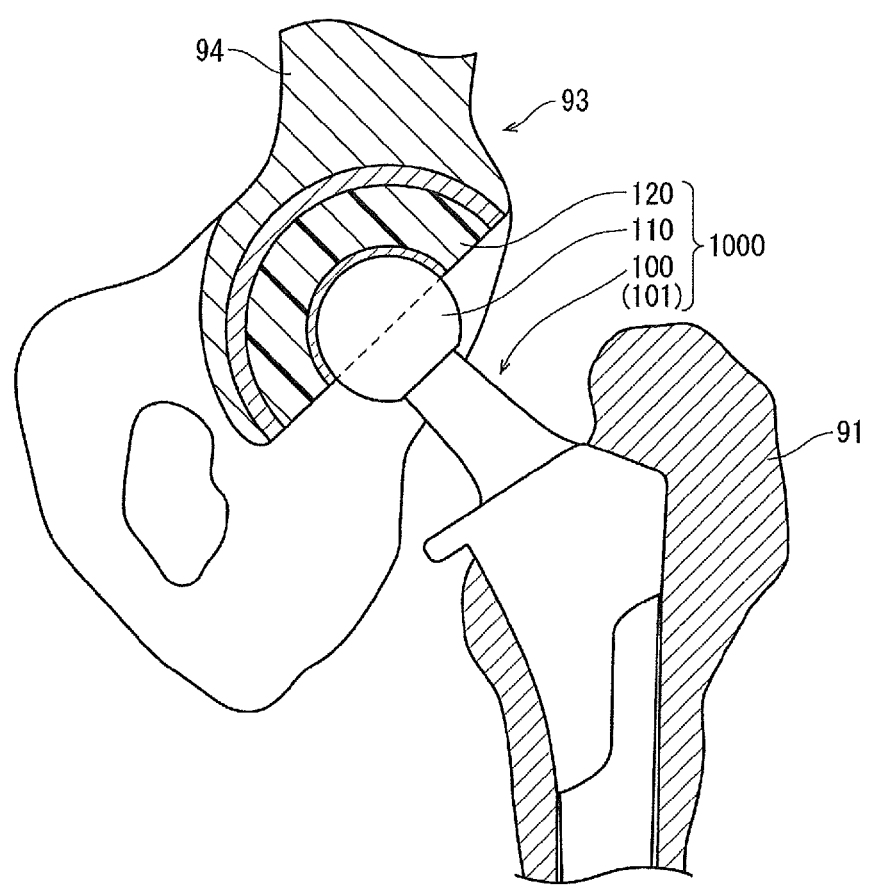
FIG. 7 is a schematic view illustrating an artificial hip joint according to an embodiment.

Referring now to FIG. 7, an example in which the artificial joint stem 100 (101) is used as a part of an artificial hip joint 1000 will be described below. The artificial hip joint 1000 may include a bone head 110 and an acetabular cup 120 in addition to the artificial joint stem 100 (101). The bone head 110 and the acetabular cup 120 may be formed of a material the same as or different from that of the base 10 of the artificial joint stem 100 (101). The artificial joint stem 100 (101) is embedded in a femur 91. The bone head 110 is disposed at an exposed portion of the artificial joint stem 100 (101). The acetabular cup 120 is fixed to an acetabular 94 of a hip bone 93. The acetabular cup 120 functions as a hip joint by fitting and sliding the bone head 110 into the depression of the acetabular cup 120.

In the present disclosure, the invention has been described above based on the various drawings and examples. However, the invention according to the present disclosure is not limited to each embodiment described above. That is, the embodiments of the invention according to the present disclosure can be modified in various ways within the scope illustrated in the present disclosure, and embodiments obtained by appropriately combining the technical means disclosed in different embodiments are also included in the technical scope of the invention according to the present disclosure. In other words, note that a person skilled in the art can easily make various variations or modifications based on the present disclosure. Note that these variations or modifications are included within the scope of the present disclosure.

REFERENCE SIGNS

2 Recessed portion
10 Base

10C Coating film region
20, 20A Coating film
21, 21A Rough surface
30 Layer member
100, 101 Artificial joint stem
200, 210 Hole
211, 211A Exposed region
220 Groove
1000 Artificial hip joint

The invention claimed is:

1. An artificial joint stem comprising:
a base having an outer surface comprising a rough surface; and
a coating film disposed on the rough surface of the base, the coating film containing a calcium phosphate-based material and an antimicrobial material,
wherein
the rough surface comprises an exposed region exposed from the coating film; and
an edge of the coating film is along an edge of the rough surface.

2. The artificial joint stem according to claim 1, wherein a surface roughness of the exposed region of the rough surface is greater than a surface roughness of the coating film.

3. The artificial joint stem according to claim 1, wherein of a whole of the rough surface, the exposed region is smaller than a region where the coating film of the rough surface is disposed.

4. The artificial joint stem according to claim 1, wherein the base comprises a lower end side and a proximal end side that is adjacent to a proximal side of a human body when the artificial joint stem is in use, and the exposed region exposed from the coating film is located only on the lower end side.

5. The artificial joint stem according to claim 1, wherein the base comprises a layer member having a surface as the rough surface of the base.

6. The artificial joint stem according to claim 5, wherein a thickness of the layer member is greater than a thickness of the coating film.

7. The artificial joint stem according to claim 1, further comprising:
at least one recessed portion disposed on a surface of the coating film.

8. The artificial joint stem according to claim 7, wherein on the surface of the coating film, a region where the at least one recessed portion is disposed is smaller than a region where the at least one recessed portion is not disposed.

9. The artificial joint stem according to claim 7, wherein the at least one recessed portion comprises at least one groove.

10. The artificial joint stem according to claim 9, wherein the at least one groove comprises a first groove with one tip located on the exposed region.

11. The artificial joint stem according to claim 9, wherein the at least one groove comprises a second groove with both ends located on the coating film.

12. The artificial joint stem according to claim 9, wherein the at least one recessed portion comprises a plurality of recessed portions disposed discontinuously from each other.

13. The artificial joint stem according to claim 7, wherein the at least one recessed portion comprises a bottom portion with a polygonal planar shape.

14. The artificial joint stem according to claim 7, wherein the at least one recessed portion increases in depth along one direction of a straight line connecting two different points of edges of the at least one recessed portion.

15. An artificial joint stem comprising:

a base having an outer surface comprising a rough surface with an edge; and a coating film disposed on the rough surface of the base, the coating film containing a calcium phosphate-based material and an antimicrobial material, wherein the rough surface comprises an exposed region exposed from the coating film; and an edge of the coating film is non-parallel to the edge of the rough surface.

16. An artificial joint stem comprising:

a base having an outer surface comprising a rough surface; and a coating film disposed on the rough surface of the base, the coating film containing a calcium phosphate-based material and an antimicrobial material, wherein the rough surface comprises an exposed region exposed from the coating film;

the outer surface comprises a surface different from the rough surface; and the coating film comprises a coating film region straddling the rough surface and the surface different from the rough surface.

17. The artificial joint stem according to claim 16, wherein the base comprises a lower end side and a proximal end side that is adjacent to a proximal side of a human body when the artificial joint stem is in use, and the coating film region is located on the lower end side of the base.

18. The artificial joint stem according to claim 16, wherein on the surface different from the rough surface, a surface roughness of the outer surface where the coating film region is located is greater than a surface roughness of a region exposed from the coating film region.

* * * * *